United States Patent [19]

Beech, Jr. et al.

[11] Patent Number: 5,073,351

[45] Date of Patent: Dec. 17, 1991

[54] PRODUCTION OF MIDDLE DISTILLATE RANGE HYDROCARBONS BY LIGHT OLEFIN UPGRADING

[75] Inventors: James H. Beech, Jr., Wilmington, Del.; Hartley Owen, Belle Mead, N.J.; Michael P. Ramage, Morrestown, N.J.; Samuel A. Tabak, Wenonah, N.J.

[73] Assignee: Mobil Oil Corporation, Fairfax, Va.

[21] Appl. No.: 322,263

[22] Filed: Mar. 13, 1989

Related U.S. Application Data

[60] Division of Ser. No. 935,374, Nov. 26, 1986, Pat. No. 4,849,186, which is a continuation-in-part of Ser. No. 699,882, Feb. 8, 1985, Pat. No. 4,720,600, which is a continuation-in-part of Ser. No. 654,348, Sep. 25, 1984, Pat. No. 4,547,612, and a continuation-in-part of Ser. No. 616,376, Jun. 1, 1984, Pat. No. 4,504,691.

[51] Int. Cl.$^5$ .......................... B01J 8/04; B01J 19/24

[52] U.S. Cl. .................. 422/190; 202/154; 203/74; 203/81; 203/DIG. 6; 422/187; 422/189; 422/234

[58] Field of Search ............ 422/187, 189, 190, 234; 202/154; 203/74, 81, DIG. 6

[56] References Cited

U.S. PATENT DOCUMENTS 4,689,205  8/1987  Gould et al. ............... 422/190 X

Primary Examiner—Jill Johnston
Attorney, Agent, or Firm—Alexander J. McKillop; Charles J. Speciale; L. G. Wise

[57] ABSTRACT

An oligomerization system is provided for upgrading lower olefins to distillate hydrocarbons, especially useful as high quality jet or diesel fuels. The olefinic feedstock is reacted over a shape selective acid zeolite, such as ZSM-5, to oligomerize feedstock olefins and further convert recycled hydrocarbons. Reactor effluent is fractionated to recover a light-middle distillate range product stream and to obtain gasoline and heavy hydrocarbon streams for recycle.

6 Claims, 5 Drawing Sheets

PRODUCTION OF MIDDLE DISTILLATE RANGE HYDROCARBONS BY LIGHT OLEFIN UPGRADING

CROSS-REFERENCE TO RELATED APPLICATION

This is a division of copending application Ser. No. 935,374, filed on Nov. 26, 1986, now U.S. Pat. No. 4,849,186, which is a continuation-in-part of application Ser. No. 699,882, filed Feb. 8, 1985 now U.S. Pat. No. 4,720,600 which is a continuation-in-part of application Ser. No. 654,348, filed Sept. 25, 1984, now U.S. Pat. No. 4,547,612 and a continuation-in-part of application Ser. No. 616,376, filed June 1, 1984, now U.S. Pat. No. 4,504,691.

FIELD OF THE INVENTION

This invention relates to a continuous technique for the manufacture of distillate range hydrocarbons, such as jet aircraft engine fuel or kerosene In particular, it provides a system for operating an olefins conversion plant wherein a oligomerization catalyst, such as shape selective medium pore crystalline zeolite of the ZSM-5 type, is employed for upgrading olefinic feedstocks containing lower alkenes at elevated temperature and pressure.

BACKGROUND OF THE INVENTION

Recent work in the field of olefin upgrading has resulted in a catalytic process for converting lower olefins to heavier hydrocarbons. Particular interest is shown in a technique wherein distillate range hydrocarbons can be synthesized over ZSM-5 type catalysts at elevated temperature and pressure to provide a product having substantially linear molecular conformations due to the ellipsoidal shape selectivity of certain medium pore catalysts.

Conversion of olefins to gasoline and/or distillate products is disclosed in U.S. Pat. Nos. 3,960,978 and 4,021,502 (Givens, Plank and Rosinski) wherein gaseous olefins in the range of ethylene to pentene, either alone or in admixture with paraffins are converted into an olefinic gasoline blending stock by contacting the olefins with a catalyst bed made up of a ZSM-5 type zeolite. In U.S. Pat. No. 4,227,992 Garwood and Lee disclose the operating conditions for the Mobil Olefin to Gasoline/Distillate (MOGD) process for selective conversion of $C_3^+$ olefins to mainly aliphatic hydrocarbons. In a related manner, U.S. Pat. Nos. 4,150,062 and 4,211,640 (Garwood et al) disclose a process for converting olefins to gasoline components.

In the process for catalytic conversion of olefins to heavier hydrocarbons by catalytic oligomerization using a medium pore shape selective acid crystalline zeolite, such as ZSM-5 type catalyst, process conditions can be varied to favor the formation of hydrocarbons of varying molecular weight. At moderate temperature and relatively high pressure, the conversion conditions favor $C_{10}^+$ aliphatic product. Lower olefinic feedstocks containing $C_2$-$C_8$ alkenes may be converted; however, the distillate mode conditions do not convert a major fraction of ethylene. A typical reactive feedstock consists essentially of $C_3$-$C_6$ mono-olefins, with varying amounts of nonreactive paraffins and the like being acceptable components.

It is a main object of this invention to provide a continuous system devised for upgrading olefins to valuable middle distillate fuel product. It is a further object to provide an operable olefins oligomerization technique to maximize production of light and middle distillate product, such as high quality jet fuel having a boiling range of about 165° to 290° C. (330°-550° F.).

SUMMARY OF THE INVENTION

A continuous system has been devised for converting a feedstock comprising lower olefins to form higher hydrocarbons, particularly distillate product. This system includes means for producing heavy hydrocarbons comprising distillate range compounds having a substantially linear molecular conformation comprising means for contacting olefinic feedstock in a catalytic reaction zone under oligomerization conditions at moderate reaction temperature and high pressure favorable to formation of high molecular weight aliphatic hydrocarbons with a shape selective medium pore acidic crystalline silicate zeolite catalyst in a reaction zone maintained under low severity conditions to prevent excessive cracking; means for recovering oligomerized hydrocarbon effluent containing middle distillate range hydrocarbon product, higher boiling hydrocarbons and lower boiling hydrocarbons; means for fractionating the effluent to obtain a distillate range product fraction, a higher boiling liquid fraction, and a lower boiling liquid fraction; and means for recycling higher and lower boiling liquid streams comprising at least a major portion of the higher and lower boiling liquid fractions for further reaction in the reaction zone.

This technique is particularly useful for producing middle distillate hydrocarbons comprising $C_9$ to $C_{16}$ aliphatic compounds having a substantially linear molecular conformation. These and other objects and features of the invention will be understood from the following detailed description and drawings.

THE DRAWINGS

DESCRIPTION OF THE PREFERRED EMBODIMENTS

Figure 1:
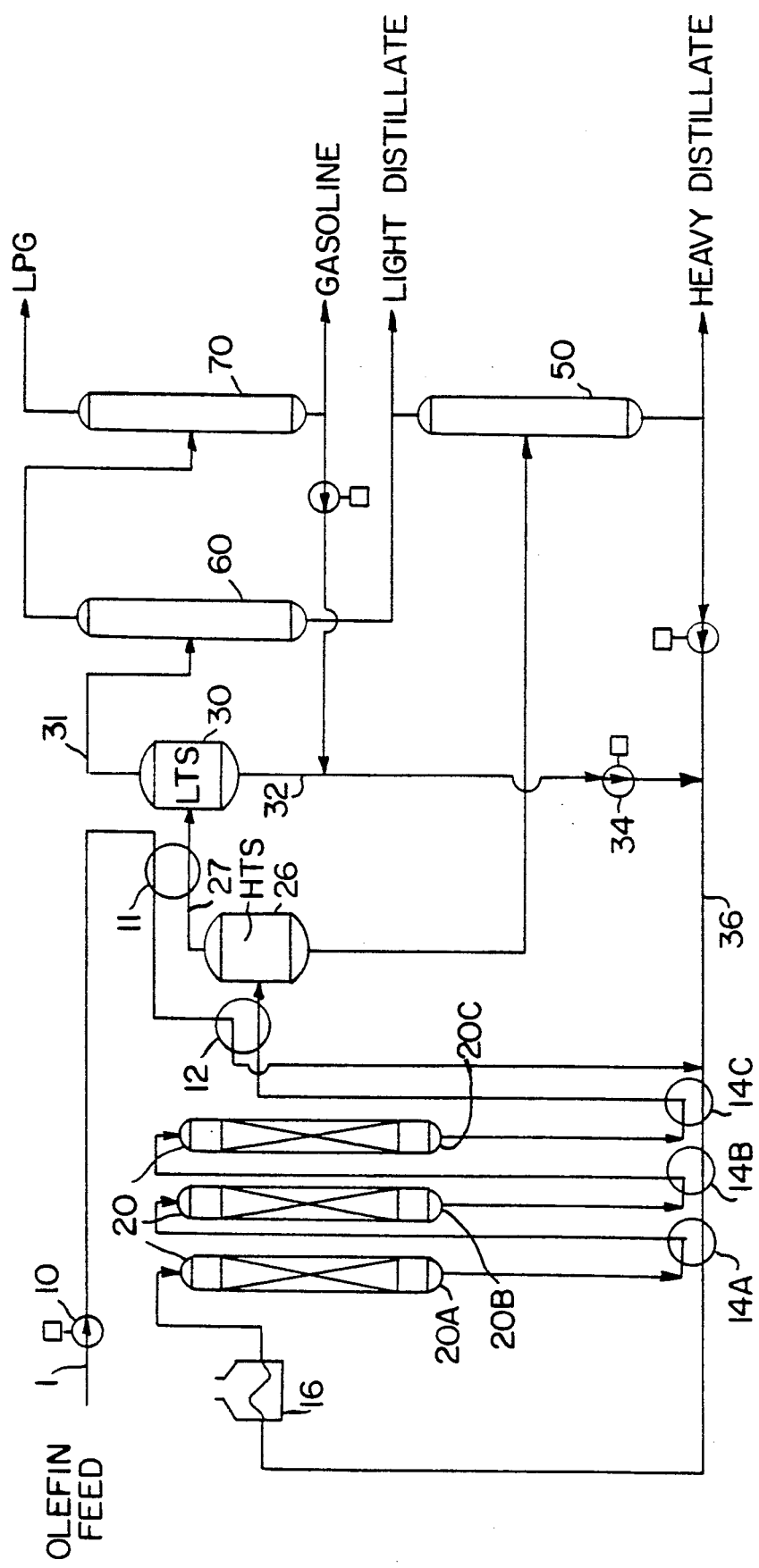
FIG. 1 is a schematic representation of a fixed bed reactor system and product separation system, according to the present invention, showing process flow streams and unit operations.

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The oligomerization/polymerization catalysts preferred for use herein include the crystalline aluminosilicate zeolites having a silica to alumina molar ratio of at least 12, preferable about 20:1 to 100:1, a constraint index of about 1 to 12 and acid cracking activity of about 50-200. Representative of the ZSM-5 type zeolites are ZSM-5, ZSM-11, ZSM-12, ZSM-23, ZSM-35 and ZSM-38. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable shape selective medium pore catalyst of fixed bed is a standard H-ZSM-5 zeolite (silica:alumina ratio=70:1) with alumina binder in the form of cylindrical extrudates of about 1-5 mm. Unless otherwise stated in this description, the catalyst shall consist essentially of this standard ZSM-5, which has an acid cracking value ($\alpha$-value) of about 160-200. Other pentasil catalysts which may be used in one or more reactor stage include a variety of medium pore shape selective (5 to 9 A) siliceous materials such as borosilicates, ferrosilicates, and/or aluminosilicates disclosed in U.S. Pat. Nos. 4,414,423, 4,417,086, 4,417,087 and 4,417,088, incorporated herein by reference.

Shape-selective oligomerization, as it applies to the conversion of $C_2$-$C_{10}$ olefins over ZSM-5, is known to produce higher olefins up to $C_{30}$ and higher. As reported by Garwood in Intrazeolite Chemistry 23, (Amer. Chem. Soc., 1983), reaction conditions favoring higher molecular weight product are low temperature (200°-260° C), high pressure (300 psig or greater), and long contact time (0.5-1 WHSV). The reaction under these conditions proceeds through the acid-catalyzed steps of (1) oligomerization, (2) isomerization-cracking to a mixture of intermediate carbon number olefins, and (3) interpolymerization to give a continuous boiling product containing all carbon numbers. The channel systems of ZSM-5 type catalysts impose shape-selective constraints on the configuration of the large molecules, accounting for the differences with other catalysts.

The following model reaction path for propylene is set forth for purposes of explanation, and it should be taken as a theoretical path, as the process is presently understood by workers in the field.

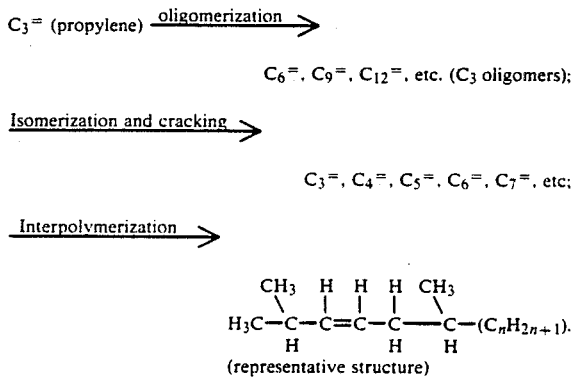

The desired oligomerization-polymerization products are $C_{10}{}^+$ substantially linear aliphatic hydrocarbons. As a result of having both forward (polymerization) and reverse (cracking), a continuous molecular weight distribution will occur in the product which can be independent of the carbon number of the starting olefin. For example, Garwood has previously shown, at constant temperature and pressure, virtually identical product distribution for feedstocks of ethylene ($C_2{}^=$), propylene ($C_3{}^=$), pentene ($C_5{}^=$), hexene ($C_6{}^=$) and decene $C_{10}{}^=$. Structurally the final product is influenced by the pore structure of the catalyst. For low carbon number products (i.e., $C_4$, $C_5$) isomer distribution is approximately at equilibrium. For the higher carbon numbers, the structure is primarily a methyl-branched straight olefinic chain, with the maximum cross section of the chain limited by the 5.4×5.6 Angstrom dimension of the largest ZSM-5 pore. At conditions chosen to maximize distillate range products ($C_{10}{}^+$) the raw aliphatic product is essentially mono-olefinic with 10% or less of the double bond in the alpha position. Overall branching is not extensive, with most branches being methyl at about one branch per four/five carbon atoms.

The flowsheet diagram of FIG. 1 shows the process relationships of the inventive process, depicting the conversion of the $C_3$-$C_6$ rich olefinic intermediate, multi-stage phase separation and recycle. Middle distillate hydrocarbons are recovered by fractionation and may be sent to a conventional hydrotreating unit for product finishing.

GENERAL PROCESS DESCRIPTION

The olefinic feedstock supply 1 is normally liquid and can be brought to process pressure by means of pump 10 and preheated by passing sequentially through a series of heat exchange means 11, 12 and reactant effluent exchangers 14C, 14B, 14A and furnace 16 prior to entering the catalytic reactor system 20.

A typical distillate mode first stage reactor system 20 is shown. A multi-reactor system is employed with inter-zone cooling, whereby the reaction exotherm can be carefully controlled to prevent excessive temperature above the normal moderate range of about 200° to 290° C. (400°-550° F.), especially in the final reaction zone While process pressure may be maintained over a wide range, usually from about 2800 to over 20,000 kPa (400-3000 psia), the preferred pressure is about 4000 to 10,000 kPa (600 to 1500 psia). The feedstock is heated to reaction temperature and carried sequentially through a series of zeolite beds 20A, B, C wherein at least a portion of the olefin content is converted to heavier distillate constituents. Advantageously, the maximum temperature differential across only one reactor is about 30° C. (T=50° F.) and the space velocity (LHSV based on olefin feed) is about 0.1 to 2, preferably about 1.0. The heat exchangers 14A and 14B provide inter-reactor cooling.

In a typical continuous process run under steady state conditions using a standard HZSM-5 catalyst, the average reactor temperature in the series of adiabatic fixed bed reactors is maintained below about 315° C. (600° F). In order to optimize formation of high molecular weight $C_9{}^+$ hydrocarbons, effluent temperature from the terminal reactor 20C is kept substantially below about 290° C. (550° F.). Catalyst in the terminal position is preferably the most active in the series, being fresh or regenerated to maintain a high alpha value. By controlling the moderate reaction temperature in the last two beds, undesired cracking of the product $C_9^+$ hydrocarbons is minimized.

The reactor effluent is cooled in exchanges 12 and 14C before fractionation. The effluent fractionation system has two main functions: (1) to provide primary means for separating suitable recycle materials and (2) to provide secondary means for recovering refined product streams of acceptable quality. The primary section is not required to provide streams of clearly defined boiling point components; and, therefore, phase separator in combination with flashing and heat exchange equipment can provide adequate recycle economically. However, the secondary fractionation function requires distinct separation according to molecular weight and boiling point, which usually dictates at least one distillation tower. While the embodiments disclosed herein include operatively connected separators, product splitters, debutanizers, etc., it is within the skill of the art to apply the inventive concept to a variety of effluent separation systems, to provide the required recycle and product streams for a continuous light olefin upgrading system according to the present invention.

The effluent mixture under process pressure or flashed enters a high temperature separator (HTS) 26, wherein higher boiling product is recovered as a liquid rich in $C_{16}^+$ hydrocarbons; while vaporizing volatile components of the effluent stream, including the light and intermediate hydrocarbons, such as $C_1$ to $C_{16}$ aliphatics. Preferably, the major portion (e.g. 50% to more than 90 wt %) of $C_{16}$ hydrocarbon components are contained in the high boiling liquid fraction. Overhead vapor is withdrawn through conduit 27, cooled indirectly by incoming feedstock in exchanger 11 to condense a major amount gasoline range hydrocarbons for recovery in the second phase separation unit 30. This condensed stream is withdrawn through conduit 32 for recycle and pressurized by pump means 34 prior to combining with feedstock in conduit 36. Advantageously, the major portion of $C_5$ to $C_8$ hydrocarbon components boiling below about 165° C. are contained in the liquified lower boiling recycle stream.

Liquid hydrocarbons rich in middle and heavy distillate are recovered from the primary separation zone 26 at process pressure, preferably about 1000 to 1500 kPa (150 to 220 psia) and passed to product splitter tower 50 for secondary fractionation to provide a middle distillate product fraction rich in $C_9$-$C_{16}$ olefins and a $C_{16}^+$ heavy distillate stream for recycle or recovery. A vapor overhead stream from the second separation zone 30 is sent directly through conduit 31 to the distillation tower 60 to provide a middle distillate bottoms stream. Gasoline rich overhead from tower 60 is further fractionated in debutanizer tower 70, which provides $C_5$-165° C. olefinic gasoline for additional recycle or product along with $C_3$-$C_4$ rich LPG.

Raw olefinic product may then be hydrotreated in a separate process step (not shown) to provide a paraffinic distillate product meeting jet fuel requirements. Details of a mild hydrogenation treatment may be obtained from U.S. Pat. No. 4,211,640, incorporated by reference, typically using Co or Ni with W/Mo and/or noble metals. The hydrotreated stream may be further fractionated for flash point stabilization.

There are several advantages to the process design. The lower boiling range hydrocarbon recycle consists essentially of $C_5$-$C_8$ hydrocarbons, with minor amounts of $C_4^-$ components. This recycle material preferably includes at least b 50% of the $C_5$ to $C_8$ hydrocarbons from the reactor effluent. Having a relatively high heat capacity, it provides a good heat sink without diminishing feedstock olefin partial pressure and thereby maintains a high olefin partial pressure at reactor inlet. The liquid recycle is economically repressurized by pumping, which requires modest power consumption.

Typical distillate mode oligomerization operations are conducted over a fixed bed of HZSM-5/alumina extrudate catalyst using the techniques described in U.S. Pat. No. 4,456,779 (Owen et al.), U.S. Pat. No. 4,433,185 (Tabak), and U.S. patent application Ser. No. 654,348 (filed 25 Sept. 1984), incorporated herein by reference. Reactor sequencing and catalyst regeneration are known in the art.

Figure 2:
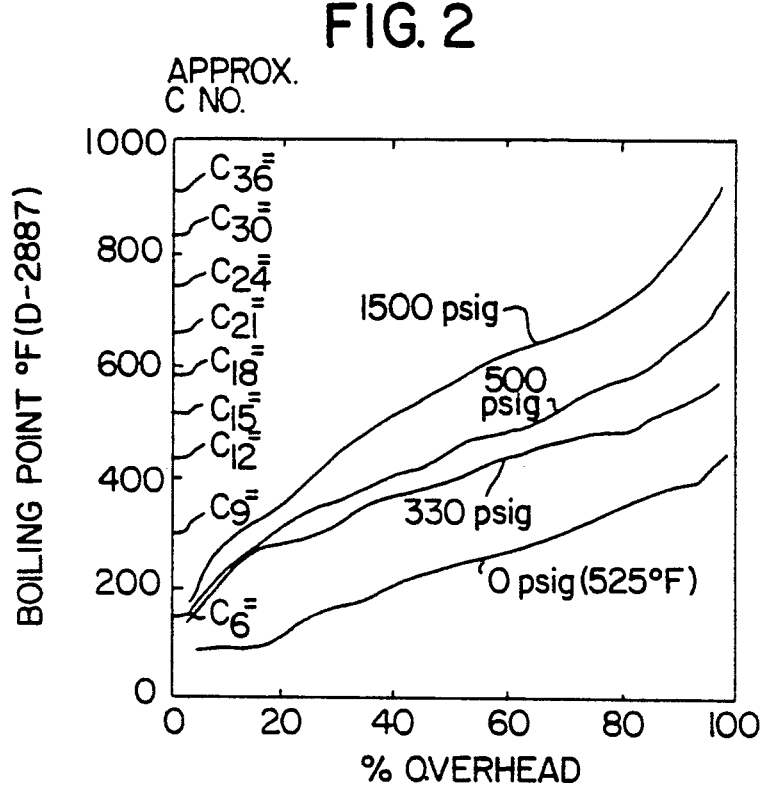
FIG. 2 is a graphic plot showing product distribution for a series of propylene conversion runs at various pressures.

In order to demonstrate the effect of pressure on the process, propylene is reacted at 204° C. and 0.4 WHSV over HZSM-5 in an isothermal reaction zone. FIG. 2 shows a correlation between boiling range of liquid product from 2400 to 10,400 kPa, with a low pressure run (274° C.) plotted for comparison. Propylene conversion is essentially complete at 204° C. under these conditions, and the liquid product includes all carbon numbers from $C_6$ to about $C_{36}$.

Figure 3:
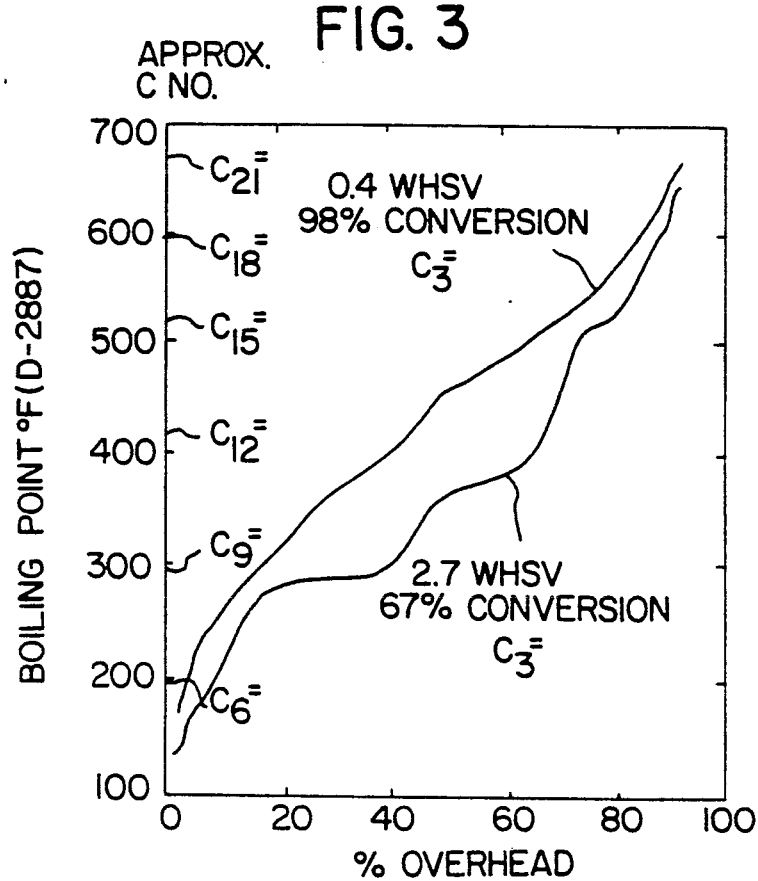
FIG. 3 is a graphic plot of propylene conversion over HZSM-5 at different space velocities.

In FIG. 3, the effect of contact time is depicted by comparing two runs using propylene feed at 204° C. and 3600 kPa. The liquid boiling plateaus in the higher space velocity run (2.7 WHSV) show evidence of oligomers, corresponding to the trimer, tetramer and pentamer of propylene formed at 67% conversion during short residence. This contrasts with the relatively smooth curve of a longer contact time (0.4 WHSV). The preferred operation with space velocity less than 1 provides essentially complete conversion of $C_3$-$C_{10}$ feedstock. It is a characteristic of the reaction path that the liquid product boiling point curve for propylene is substantially similar to that of a $C_{10}$ (1-decene) feed, at low space velocity (0.1 to 0.5), 277° C. (530° F.) reaction temperature. This suggests that the two widely different charge olefins undergo a common intermediate stage.

Figure 4:
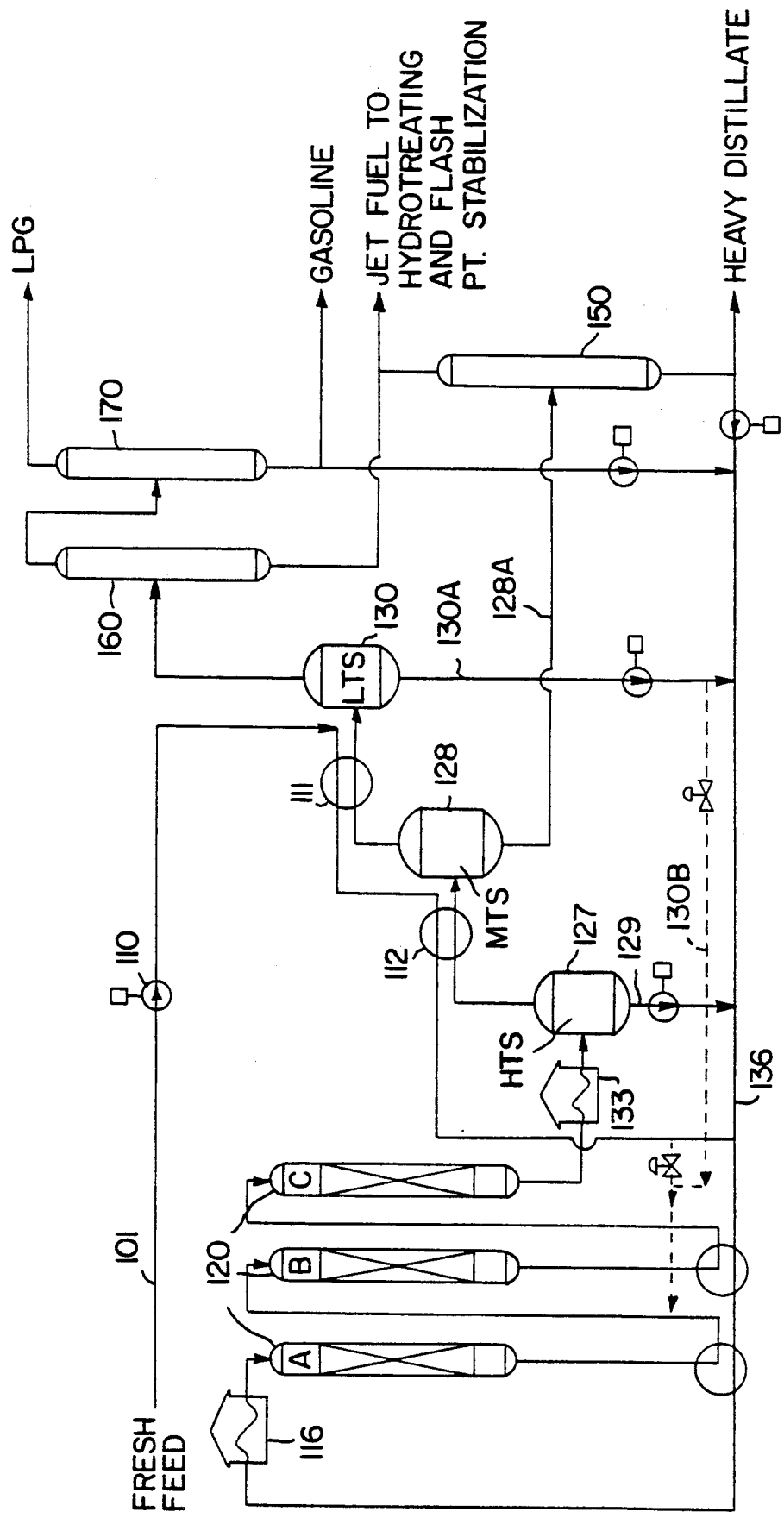
FIG. 4 is a schematic process diagram of an alternative embodiment of the invention.

An alternate embodiment of the inventive process is depicted in FIG. 4, which is a flow sheet for a continuous olefins upgrading plant employing a fixed bed catalytic reactor. Simplified effluent fractionation and recycle streams are shown schematically, with reactor transfer and other details being omitted. Referring to FIG. 4, fresh olefinic feed 101 is pressurized and preheated via exchangers 111, 112. The fresh lower olefin feed may be fed directly to the primary reactor 120A combined with recycle 136 and heated in furnace 116 to reaction temperature. Optionally, the feedstock may be diverted around reactor 120A to position B. The feedstock is passed over standard ZSM-5 catalyst in a series of continuous downflow vertical fixed bed reactors 120. The average reactor temperature is incrementally decreased from about 315° C. (600° F.) to 260° C. (500° F.), or higher, thereby favoring cracking in the first reactor A and oligomerization in the last reactor C. A series of high, middle and low temperature phase separators 127, 128, 130 are employed to recover a high boiling liquid recycle stream 129 and a middle distillate-rich liquid product stream 128A, which is passed to distillation tower 150 for splitting into heavy distillate (290° C.+) and light distillate streams. The light distillate may be further treated by hydrogenation and flash point stabilization in a known manner. Gasoline and LPG are recovered by fractionating the overhead vapor from the low temperature separator, from which another recycle stream 130A is taken, which stream is rich in $C_5$ to $C_8$ hydrocarbons. Optionally the light hydrocarbon recycle from low temperature separator 130 may be sent to the low temperature reactor(s) via conduit 130B together with diverted feedstock olefins, bypassing the higher temperature first reactor A and thereby avoiding substantial cracking.

In the following examples the average reactor temperature is maintained within the range of 205° to 290° C. (400° to 550° F.), and a space velocity (WHSV based on feed olefin) of about 0.6 to 1.0. Three different operating pressures are employed in successive continuous runs at about 4200 kPa (600 psig), 5600 kPa (800 psig) and at 10400 kPa (1500 psig). Under these conditions, a feedstock consisting of 10.7 weight percent propane, 27 wt % propylene, 26.2 wt % isobutane and 36.1 wt % butylene is converted.

Figure 5:
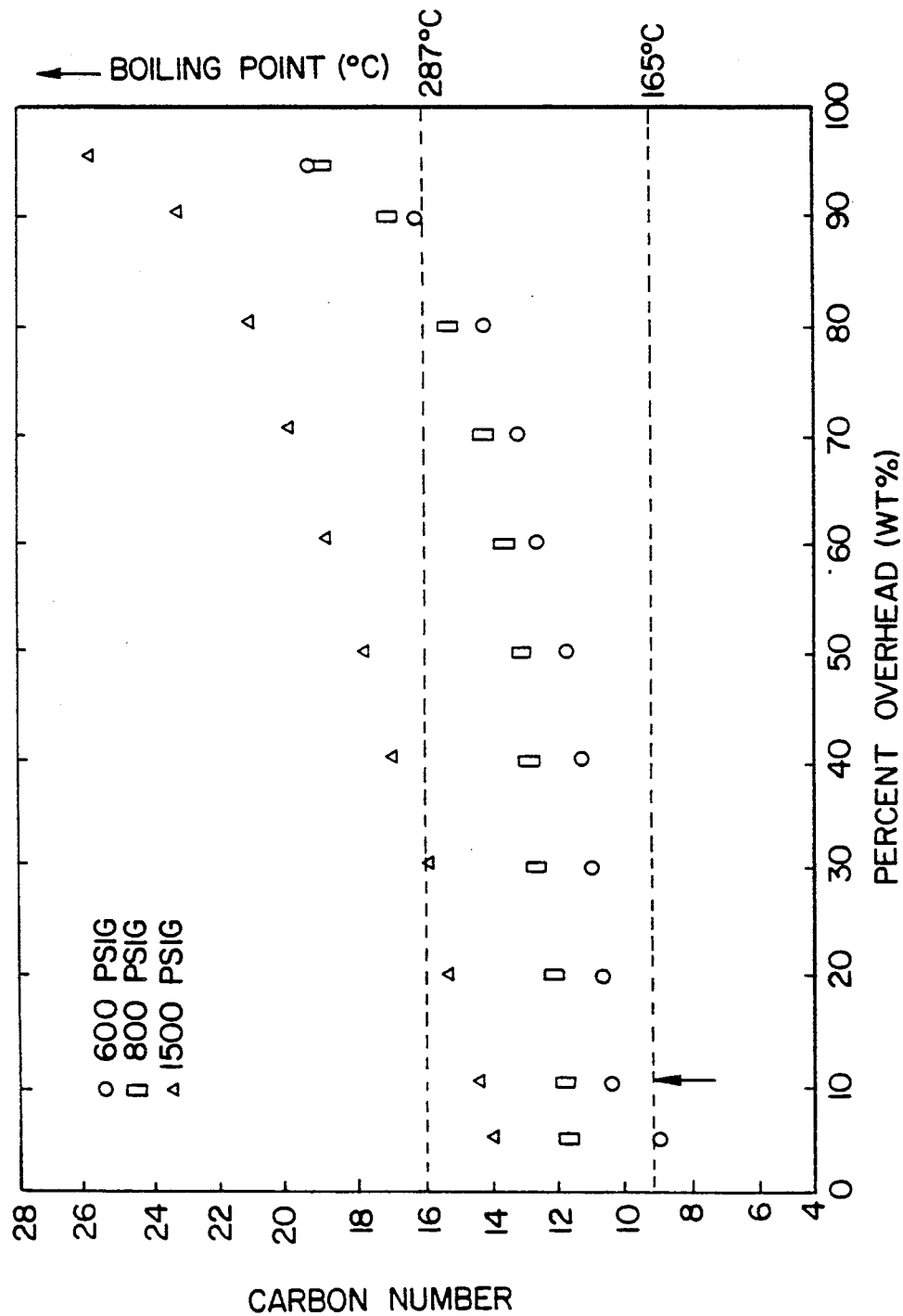
FIG. 5 is a graphic plot of product distribution by carbon number at various pressures.

In FIG. 5, the results of the three runs are plotted to show the product distribution in the reactor effluent, employing gasoline recycle. Optimum jet fuel distillate hydrocarbons are produced in the $C_9$ to $C_{16}$ range, corresponding to a normal boiling point of about 165° C. to 290° C. When the higher boiling 290°+ C. hydrocarbons are reprocessed under the same reaction conditions a single pass conversion run yields an average increase of about 23 wt. % to light distillate (165°–290° C.) and 8 wt. % $C_5$–165° C. gasoline range components in the effluent. The product distribution of reprocessed 290°+ C. hydrocarbons is shown in Table I.

TABLE I

| Yield from Reprocessed Heavy Distillate, 290°+ C. (550° F.−) | | | | |
|---|---|---|---|---|
| | DAYS ON STREAM | | | |
| | 6 | 7 | 8 | 9 |
| OPERATING CONDITIONS | | | | |
| AVE. REAC. TEMP., F. | 500 | 520 | 541 | 561 |
| REAC. PRESS., PSIG | 600 | 600 | 600 | 600 |
| LHSV, (TOTAL) | 1.00 | 1.00 | 1.00 | 1.00 |
| WHSV, (TOTAL) | 1.35 | 1.35 | 1.35 | 1.35 |
| PRODUCT DISTRIBUTION (WT %) | | | | |
| C4 | 0.61 | 0.89 | 1.27 | 1.63 |
| C5+ −330 F. | 6.74 | 7.72 | 7.40 | 9.17 |
| 330 F.-550 F. | 24.90 | 23.84 | 22.83 | 21.80 |
| 550 F.+ | 67.74 | 67.55 | 68.50 | 67.40 |

Typical product specifications for jet fuels are given below.

TABLE II

| Jet Fuel Volatility Specifications | | | |
|---|---|---|---|
| JP4 (MIL-T-5624L) | JP5 (MIL-T-5624L) | JP7 (MIL-T-38219) | JET A |
| 10% BP (D86), °F. | NS | 401 (max) | 385 (min) | 400 (max) |
| 90% BP (D86), °F. (max) | 473 | NS | 500 | NS |
| End Point (D86), °F. (max) | 518 | 554 | 550 | 572 |
| Flash Point, °F. (min) | NS | 140 | 140 | 100 |

Figure 6:
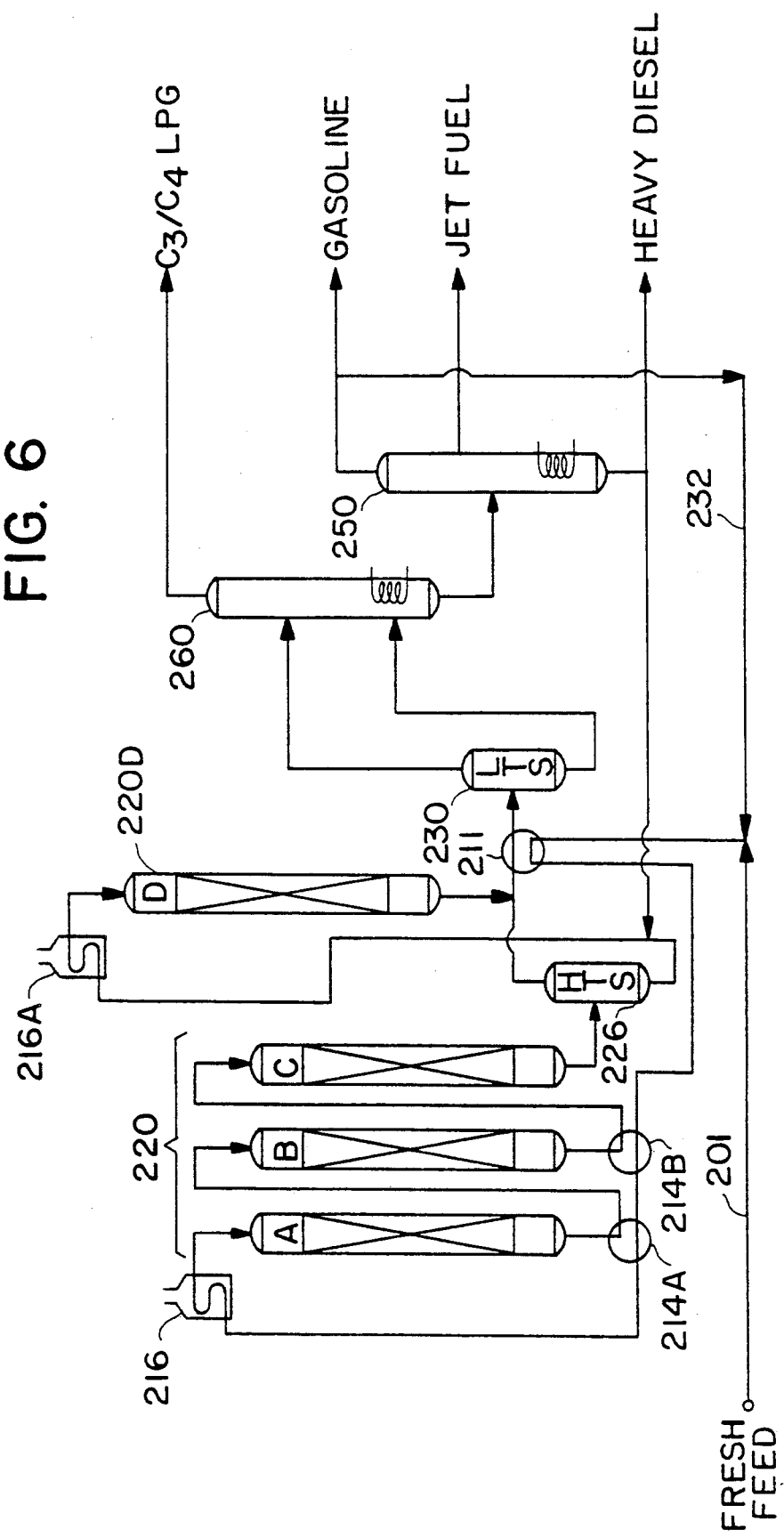
FIG. 6 is a process flow sheet for an alternative embodiment.

A continuous system for upgrading lower olefin feedstock to higher hydrocarbons is depicted in FIG. 6, wherein ordinal numbers correspond with elements in FIG. 1. Reactor means 220A, B, C is provided for contacting the feedstock, via conduit 201, exchangers 211, 214A and B, with a shape selective medium pore acid zeolite catalyst under reaction conditions at elevated temperature in a pressurized reactor system 220 comprising a series of catalytic reactor beds A, B, C to convert olefins. The heat exchangers 214 A, B provide means for incrementally decreasing reactor temperature from a first reactor bed 220A in the series to terminal reactor bed 220C to promote oligomerization in the last reactor bed. First HTS separation means 226 separates reactor effluent to separate volatile light and middle distillate hydrocarbon components into a first vapor phase stream and recovers heavy liquid for catalytic cracking in reactor unit 220D, maintained at a temperature of at least about 400° C. under conversion conditions to degrade the heavy hydrocarbons for recycle of cracked components via separator 230. The heavy liquid stream contains at least 50% of those $C_{16}$+ hydrocarbons recovered in the reactor effluent.

Second LTS separation means 230 condenses a portion of the first vapor phase stream to recover a dominant portion of a light olefinic C6–C8 stream. This can be recycle via distillation towers 250, 260 for further reaction in one or more serial reactor beds to promote oligomerization. The light recycle stream comprises a major portion of $C_6$ to $C_8$ hydrocarbons recovered in the reactor effluent. Fractionation towers 250 and 260 provide means for distilling the intermediate liquid product stream recovered from the second separation means to obtain a middle distillate product stream(eg-jet fuel) consisting essentially of substantially linear $C_9$-$C_{16}$ aliphatic hydrocarbons, along with minor amounts of LPG, gasoline and heavy diesel fuels, for instance.

The reactor system depicted contains multiple downflow adiabatic catalytic zones in each reactor zone. The liquid hourly space velocity (based on total fresh feedstock) is about 1 LHSV. In the preferred distillate mode the inlet pressure to the first oligomerization reactor is about 4200 kPa (600 psig total), with an olefin partial pressure of at least about 1200 kPa. Based on olefin conversion of 50% of ethene, 95% for propene, 85% for butene-1 and 75% for pentene-1, and exothermic heat of reaction is estimated at 450 BTU per pound of olefins converted. When released uniformly over the reactor beds, a maximum T in each reactor is about 30° C.

Preferably the ZSM-5 catalyst is kept on stream until the coke content increases from 0% at the start of cycle (SOC) until it reaches a maximum of 30 weight % at the end of cycle (EOC) at which time it is regenerated by oxidation of the coke deposits. Typically, a minimum 30 day total cycle can be expected between regenerations. The reaction operating temperature depends upon its serial position. The system is operated advantageously in increasing the operating temperature of the first reaction (Position A) from about 230°-255° C. (SOC) to about 270° C.-295° C. (EOC) at a catalyst aging rate of 3°-6° C./day. Reactors in the second and subsequent Positions (B, C, etc) are operated at the same SOC temperature; however, the lower aging rate (e.g. −3° C./day) in continuous operation yields a lower EOC maximum temperature (e.g.—about 275° C.) after about 7 days on stream. The end of cycle is signalled when the outlet temperature of the reactor in Position A reaches its allowable maximum. At this time the inlet temperature is reduced to start of cycle levels in order to avoid excessive coking over the freshly regenerated catalyst when a reactor containing active catalyst is brought on-line, after having been brought up to reaction pressure with an effluent slip stream.

Partially deactivated catalyst from Position A is useful for cracking at higher temperatures (e.g. −400° C.

to 600° C.) in Position D prior to cyclic regeneration. Regeneration of coked catalyst in situ may be effected by a procedure described in U.S. Pat. No. 4,456,779 (Owen et al) and U.S. Pat. No. 4,560,536 (Tabak). A programmable logic controller may be employed to control the sequencing of valve operations during all stages of reactor system operation. When regeneration is completed, the reactor is blocked off from the regeneration loop and brought up to reaction pressure with a slip stream from the process reactor effluent line. To reconnect the regenerated reactor in the proper serial position when full flow is established in the regenerated reactor in Position C, reactor C is paralleled with preceding reactor B. receiving flow from the first reactor A, etc. The partially deactivated catalyst bed is transferred from Position A to cracking operation in Position D. Finally the fully coked catalyst bed is blocked in, depressured, and repressured with nitrogen, then opened to the regeneration circuit. Thus each reactor will move from Position C to Position B to Position A to Position D before being taken off-line for catalyst regeneration.

Various modifications can be made to the system, especially in the choice of equipment and non-critical processing steps. While the invention has been described by specific examples, there is no intent to limit the inventive concept as set forth in the following claims.

What is claimed is:

1. In a continuous system for upgrading lower olefin feedstock to higher hydrocarbons including means for combining olefinic feedstock with a pressurized liquid diluent stream comprising $C_5^+$ olefins, reactor means for contacting the diluted feedstock with a shape selective medium pore acid zeolite catalyst under reaction conditions at moderate temperature in a pressurized reactor system comprising a series of catalytic reactor beds to convert olefins and recover reactor effluent at reaction conditions; the improvement which comprises:

means for incrementally decreasing reactor temperature from a first reactor bed in the series to a last reactor bed to promote oligomerization in the last reactor bed; and first separation means operatively connected to receiver effluent from said last reactor bed for separating reactor effluent in a primary phase separation zone to vaporize light and middle distillate hydrocarbon components into a first vapor phase stream and recover from the primary separation zone a heavy liquid hydrocarbon recycle stream, said heavy liquid stream containing at least 50% of those $C_{16}^+$ hydrocarbons recovered in the reactor effluent;

recycle means for passing the heavy liquid hydrocarbon recycle stream from said first separation means to said first reactor bed, maintained under conditions to degrade heavy hydrocarbons;

second separation means operatively connected to receive said first vapor phase stream for condensing a light portion of the first vapor phase and recovering a dominant portion of a light olefinic recycle stream as an intermediate liquid product stream for further reaction in a lower temperature serial reactor bed in said series of reactor beds to promote oligomerization, said light recycle stream comprising a major portion of $C_6$ to $C_8$ hydrocarbons recovered in the reactor effluent; and fractionation means for distilling the intermediate liquid product stream recovered from the second separation means to obtain a distillate product stream consisting essentially of substantially linear $C_9$–$C_{16}$ aliphatic hydrocarbons.

2. A continuous system for upgrading lower olefin feedstock to higher hydrocarbons comprising reactor means for contacting the feedstock with a shape selective medium pore acid zeolite catalyst under reaction conditions at elevated temperature in a pressurized reactor system comprising a series of catalytic reactor beds to convert olefins and recover reactor effluent at reaction conditions; the improvement which comprises:

means for incrementally decreasing reactor temperature from a first reactor bed in the series to a last reactor bed to promote oligomerization in the last reactor bed; and first separation means operatively connected to receive effluent from said last reactor bed for separating reactor effluent to vaporize light and middle distillate hydrocarbon components into a first vapor phase stream and recover a heavy liquid hydrocarbon recycle stream, said heavy liquid stream containing at least 50% of those $C_{16}^-$ hydrocarbons recovered in the reactor effluent;

recycle means for passing the heavy liquid hydrocarbon recycle stream from said first separation means to said first reactor bed, maintained under conditions to degrade heavy hydrocarbons;

second separation means operatively connected to receive said first vapor phase stream for condensing a light portion of the first vapor phase and recovering a dominant portion of a light olefinic vapor as an intermediate liquid product stream recycle stream for further reaction in a lower temperature serial reactor bed in said series of reactor beds to promote oligomerization, said light recycle stream comprising a major portion of $C_6$ to $C_8$ hydrocarbons recovered in the reactor effluent; and fractionation means for distilling the intermediate liquid product stream recovered from the second separation means to obtain a distillate product stream consisting essentially of substantially linear $C_9$–$C_{16}$ aliphatic hydrocarbons.

3. A cyclic reactor system for catalytic upgrading of olefinic hydrocarbon feedstock in a serially connected multiple catalyst zone reactor system comprising fixed catalyst bed pressurized reactors each having a porous bed zone of conversion catalyst particles, which comprises:

first stage plural serial reactor means for contacting the feedstock in a first catalyst zone at moderately elevated temperature under conditions favorable for conversion of a first reactor stream;

means for separating a first stage effluent stream into a light olefinic hydrocarbon recycle stream, at $C_9$–$C_{16}$ product stream and a second heavier hydrocarbon stream containing $C_{16}^+$ hydrocarbons;

fluid handling means for recycling at least a portion of the light olefinic hydrocarbon stream to an intermediate reactor in said first stage reactor means;

fixed bed cracking reactor means containing a porous bed of partially deactivated conversion catalyst particles for contacting the heavier hydrocarbon stream from the first stage separation means at elevated cracking temperature under conditions favorable for conversion of the heavier hydrocarbons;

cyclic fluid handling means for connecting the first stage serial reactors in operative fluid flow relationship whereby fresh or regenerated catalyst in a first stage terminal reactor position receives effluent from at least one preceding first stage reactor operating at moderately elevated oligomerization temperature, said preceding first stage reactor containing catalyst of less activity than said catalyst in the first stage terminal reactor;

fluid handling means for sequencing reactor system effluent flow to reconnect a preceding first stage reactor in position of said cracking reactor to receive the heavier hydrocarbon stream;

means for increasing temperature in said previously preceding first stage reactor to cracking temperature conditions;

means for removing an inactivated catalyst reactor from preceding reactor from cracking reactor conversion service and connecting said inactivated catalyst reactor in fluid flow relationship with a catalyst regeneration loop for catalyst reactivation;

means for advancing the terminal reactor in the first stage to a preceding serial position in the first stage; and said fluid handling means including means for adding a fresh or regenerated catalyst reactor in the first stage terminal position.

4. A continuous system for producing heavy hydrocarbons comprising distillate range compounds having a substantially linear molecular conformation from lower olefins, comprising multi-zone plural reactor means for contacting olefinic feedstock in a series of catalytic reaction zones with a shape-selective medium pore acidic crystalline silicate zeolite catalyst under low severity conditions to prevent excessive cracking;

heating and pressure means for maintaining in the reaction zone oligomerization conditions of moderate temperature and high pressure favorable to formation of high molecular weight aliphatic hydrocarbons;

separation means comprising primary and secondary phase separation means for recovering oligomerized hydrocarbon effluent containing middle distillate range hydrocarbons, high boiling hydrocarbons and lower boiling hydrocarbons;

means for fractionating the effluent to obtain a distillate range product fraction, a high boiling range liquid fraction and a lower boiling liquid fraction;

fluid handling means for recyciing at least a portion of lower boiling liquid fraction to an intermediate reactor zone in the multi-zone reactor means for further conversion therein; and fluid handling means for recycling at least a major portion of the higher boiling liquid fraction for further reactor in a primary reaction zone of said multi-zone reactor means.

5. The system of claim 4 wherein the multi-zone reactor system comprises a series of primary, intermediate and terminal operatively connected fixed bed adiabatic catalytic reactors, with inter-reactor cooling, and including means for passing recycled heavy liquid hydrocarbon through substantially all of the multi-zone reactor system.

6. The system of claim 4 wherein the crystalline silicate zeolite catalyst comprises aluminosilicate having the structure of HZSM-5.

* * * * *